United States Patent
Vikal et al.

(10) Patent No.: US 10,846,847 B2
(45) Date of Patent: Nov. 24, 2020

(54) METHOD AND APPARATUS FOR GENERATING QUANTITATIVE DATA FOR BILIARY TREE STRUCTURES

(71) Applicant: Perspectum Limited, Oxford (GB)

(72) Inventors: Siddharth Vikal, Oxford (GB); John Michael Brady, Oxford (GB)

(73) Assignee: Perspectum Limited, Oxford (GB)

( * ) Notice: Subject to any disclaimer, the term of this patent is extended or adjusted under 35 U.S.C. 154(b) by 31 days.

(21) Appl. No.: 16/092,281

(22) PCT Filed: Mar. 28, 2017

(86) PCT No.: PCT/EP2017/057302
§ 371 (c)(1),
(2) Date: Oct. 9, 2018

(87) PCT Pub. No.: WO2017/178226
PCT Pub. Date: Oct. 19, 2017

(65) Prior Publication Data
US 2019/0147590 A1    May 16, 2019

(30) Foreign Application Priority Data

Apr. 12, 2016 (GB) .................................. 1606282.0

(51) Int. Cl.
*G06K 9/00* (2006.01)
*G06T 7/00* (2017.01)
(Continued)

(52) U.S. Cl.
CPC ............ *G06T 7/0012* (2013.01); *A61B 5/055* (2013.01); *A61B 5/4244* (2013.01); *G06T 7/12* (2017.01);
(Continued)

(58) Field of Classification Search
CPC ......... G06T 7/0012; G06T 7/162; G06T 7/62; G06T 7/12; G06T 2200/04;
(Continued)

(56) References Cited

U.S. PATENT DOCUMENTS

| 8,229,186 B2 * | 7/2012 | Milstein | .................. G06T 7/181 |
| | | | 382/128 |
| 2008/0273777 A1 * | 11/2008 | Luboz | ..................... G06T 17/20 |
| | | | 382/130 |

FOREIGN PATENT DOCUMENTS

| WO | 2007/002562 A1 | 7/2007 |
| WO | 2010/129911 A1 | 11/2010 |

OTHER PUBLICATIONS

Rajasvaran Logeswaran: 11A Computer-aided Multidisease Diagnostic System Using MRCP11, Journal of Digital Imaging; The Journal of the Society for Computer Applications in Radiology, Springer-Verlag, NE, vol. 21, No. 2, Mar. 8, 2007 (Mar. 8, 2007), pp. 235-242, XP019596191, ISSN: 1618-727X the whole document.

* cited by examiner

*Primary Examiner* — Dhaval V Patel
(74) *Attorney, Agent, or Firm* — Optimus Patents US, LLC

(57) ABSTRACT

A method (200) and apparatus (1100) for generating quantitative data for biliary tree structures from volumetric medical imaging scan data. The method comprises performing segmentation (230; 300) of a volume of the medical imaging scan data to identify tubular biliary structures within the volume of the medical imaging scan data; for at least one segmented tubular biliary structure within the volume of the medical imaging scan data, computing (240; 800) at least one set of quantitative structural parameters for at least one location along the length of the tubular biliary structure; and outputting (250) quantitative biliary tree data (Continued)

comprising the at least one set of quantitative structural parameters for the at least one segmented tubular biliary structure.

36 Claims, 9 Drawing Sheets

(51) Int. Cl.
*G06T 7/12* (2017.01)
*G06T 7/162* (2017.01)
*G06T 7/62* (2017.01)
*A61B 5/055* (2006.01)
*A61B 5/00* (2006.01)

(52) U.S. Cl.
CPC ............... *G06T 7/162* (2017.01); *G06T 7/62* (2017.01); *A61B 2576/02* (2013.01); *G06T 2200/04* (2013.01); *G06T 2207/10088* (2013.01); *G06T 2207/30056* (2013.01); *G06T 2207/30172* (2013.01)

(58) Field of Classification Search
CPC . G06T 2207/30172; G06T 2207/30056; G06T 2207/10088; G06T 2207/10068; G06T 2207/10064; G06T 7/10; A61B 5/4244; A61B 5/055; A61B 2576/02
See application file for complete search history.

METHOD AND APPARATUS FOR GENERATING QUANTITATIVE DATA FOR BILIARY TREE STRUCTURES

FIELD OF THE INVENTION

This invention relates to a method and apparatus for generating quantitative data for biliary tree structures. In particular to a method and apparatus for generating quantitative data for biliary tree structures from volumetric medical imaging scan data.

BACKGROUND OF THE INVENTION

For the diagnosis of certain liver diseases, it is often critical for the diagnosing clinician to obtain an accurate assessment of the biliary tree. For example, FIG. 1 illustrates the recommendations for diagnosing Primary Sclerosing Cholangitis (PSC) as documented in the American Association for the Study of Liver Diseases (AASLD) practice guidelines.

Upon a cholestatic biochemical profile indicating the possible presence of PSC within a patient's liver, the AASLD guidelines recommend an ultrasound imaging scan be performed that can enable the clinician to observe biliary duct wall thickening and/or focal biliary duct dilatations.

If the ultrasound scan is non-diagnostic (i.e. the clinician is unable to ascertain from the ultrasound scan one way or the other whether PSC is present within the patient's liver), the AASLD guidelines recommend a Magnetic Resonance Cholangio-Pancreatography (MRCP) imaging scan. MRCP is a non-invasive MRI technique based on heavily T2-weighted pulse sequences. As a result, stationary fluids such as bile and pancreatic secretions, which have long T2 relaxation times, exhibit high signal intensity, whereas solid organs, which have shorter T2 relaxation times, have low signal intensity. Thus, an MRCP scan can provide the clinician with a view of biliary ducts within a patient's liver, enabling the clinician to detect Large Duct PSC (i.e. the presence of PSC within larger biliary ducts).

If the MRCP scan is non-diagnostic, the AASLD guidelines recommend Endoscopic Retrograde Cholangio-Pancreatography (ERCP). ERCP is a procedure that combines the use of endoscopy and fluoroscopy (involving X-rays). For ERCP, the patient is sedated or anaesthetized, after which an endoscope is inserted through the mouth, into the stomach, then through the pylorus into the duodenum where the opening of pancreatic duct exists. Then, yet another catheter is inserted through the endoscope, and radiographic contrast is injected into the biliary ducts. Fluoroscopy is then used to look for blockages or lesions within the biliary ducts. ERCP also provides the clinician with a view of biliary ducts within the patient's liver, enabling the clinician to detect Large Duct PSC.

If either of the MRCP or ERCP procedures indicates the liver is normal (i.e. no Large Duct PSC detected), because of the cholestatic biochemical profile indicating the possible presence of PSC within the liver, the AASLD guidelines recommend a liver biopsy for diagnosing Small Duct PSC, which is difficult to detect using conventional MRCP and ERCP techniques.

Conventional analysis of MRCP data involves presenting a clinician with acquired native data and/or maximum intensity projection (MIP) reconstructions of the native data. The clinician is then required to examine visually the presented data in order to view structures including biliary ducts and the like that may be visible within the presented data. Native data is typically displayed in a strictly 2-dimensional manner, that is to say a projection of the 3-dimensional information, restricting the clinician to viewing a single 2-dimensional 'slice' at any one time. MIP is a volume rendering method for 3-dimensional data that projects in the visualization plane the voxels with maximum intensity that fall in the way of parallel rays traced from the viewpoint to the plane of projection. MIP visualization suffers from a lack of depth information and occlusion related problems. For example, the small ducts can overlap larger ducts and would be hardly visible.

Both AASLD and EASL (European Association for the Study of the Liver) guidelines note that patients with early changes of PSC may be missed by MRCP, for example as a result of the MRCP views being sub-optimal, with "Diagnostic accuracy of magnetic resonance and endoscopic retrograde cholangiography in primary sclerosing cholangitis", Berstad A E, Aabakken L, Smith H J, Aasen S, Boberg K M, Schrumpf E, reporting that the depiction of biliary ducts may be poorer in MRCP than in ERCP.

However, clinicians may be reluctant to proceed with an ERCP in the assessment of cholestasis due to its invasive nature and the use of x-radiation, and so PSC has likely been an underdiagnosed condition ["EASL clinical practice guidelines", European Association for the Study of the Liver, Hepatology 2009; 51:237-267].

Indeed, it is generally desirable to avoid invasive diagnostic procedures such as ERCP and liver biopsies where possible. As such, there is a need for an improved non-invasive diagnostic technique that enables a clinician to detect liver diseases, and more generally an improved non-invasive diagnostic technique for providing a clinician with an accurate assessment of the biliary tree.

SUMMARY OF THE INVENTION

According to example embodiments of a first aspect of the invention there is provided a method of generating quantitative data for biliary tree structures from volumetric medical imaging scan data. The method comprises performing segmentation of a volume of the medical imaging scan data to identify tubular biliary structures within the volume of the medical imaging scan data, for at least one segmented tubular biliary structure within the volume of the medical imaging scan data computing at least one set of quantitative structural parameters for at least one location along the length of the tubular biliary structure and outputting quantitative biliary tree data comprising the at least one set of quantitative structural parameters for the at least one segmented tubular biliary structure.

Advantageously, by generating such quantitative biliary tree data comprising the generated quantitative structural parameters from volumetric medical imaging scan data, a clinician may be provided with enhanced information relating to the biliary tree of a patient that enables the clinician to more accurately and reliably assess the pathology of the patient's biliary tree, and in particular to more accurately and reliably assess topological and structural features of the biliary tree such as the presence of strictures and dilatations. In this manner, embodiments of the present invention provide an improved non-invasive diagnostic technique that enables a clinician to detect liver diseases, and more generally an improved non-invasive diagnostic technique for providing a clinician with an accurate assessment of the biliary tree.

In some optional embodiments of the invention, the set of quantitative structural parameters may comprise at least one parameter representative of at least one of:
- a centre-line position of the at least one segmented tubular biliary structure at the at least one location;
- a centre-line orientation of the at least one segmented tubular biliary structure at the at least one location;
- a radius of the at least one segmented tubular biliary structure at the at least one location;
- a diameter of the at least one segmented tubular biliary structure at the at least one location;
- a cross-sectional orientation of the at least one segmented tubular biliary structure at the at least one location;
- a cross-section profile of the at least one segmented tubular biliary structure at the at least one location;
- an indication of the presence of a branching point for the at least one segmented tubular biliary structure at the at least one location; and
- an orientation of a branching point for the at least one segmented tubular biliary structure at the at least one location.

In some optional embodiments of the invention, the method may comprise determining centre-line positions at a plurality of locations along the length of the at least one segmented tubular biliary structure.

In some optional embodiments of the invention, determining centre-line positions for the at least one segmented tubular biliary structure may comprise:
- identifying a starting centre-line point for the at least one segmented tubular biliary structure;
- identifying an ending centre-line point for the at least one segmented tubular biliary structure; and
- incrementally from the starting centre-line point, determining successive centre-line points for the at least one segmented tubular biliary structure until the ending centre-line point is reached.

In some optional embodiments of the invention, a successive centre-line point may be determined by:
- identifying a set of viable successor points;
- evaluating a cost function for each point within the set of viable successor points; and
- selecting a successive centre-line point from the set of viable successor points based on the cost functions therefor.

In some optional embodiments of the invention, the method may further comprise, for each of the plurality of locations along the length of the at least one segmented tubular biliary structure, determining a tube-width estimation for the at least one segmented tubular biliary structure.

In some optional embodiments of the invention, the tube-width estimation for each location may be computed by determining a cross-sectional orientation of the at least one segmented tubular biliary structure at the respective location and determining a tube-width estimation for the at least one segmented tubular biliary structure in the determined cross-sectional orientation.

In some optional embodiments of the invention, the method may further comprise detecting patterns of change within the at least one segmented tubular structure based on the tube-width estimations along the length of the at least one segmented tubular structure.

In some optional embodiments of the invention, the method may comprise detecting patterns of change within the at least one segmented tubular structure by applying at least one pattern detection window to the tube-width estimation data. For example, the method may comprise detecting at least one of:
- strictures;
- dilatations; and
- beading.

In some optional embodiments of the invention, the method may comprise identifying a first tubular biliary structure within the volume of the medical imaging scan data, determining branch node locations along the length of the first tubular biliary structure, and identifying further tubular biliary structures branching off from the branch nodes along the length of the first tubular biliary structure.

In some optional embodiments of the invention, the method may comprise recursively identifying further tubular biliary structures branching off from identified tubular biliary structures to derive a hierarchical biliary tree structure.

In some optional embodiments of the invention, the method may comprise computing at least one set of quantitative structural parameters for each location along the length of each identified tubular biliary structure.

In some optional embodiments of the invention, the method may comprise performing tubular enhancement on the volumetric medical imaging scan data to derive at least one tubeness measure for each voxel within the volumetric medical imaging scan data, and performing segmentation of the medical imaging scan data to identify tubular biliary structures based at least partly on the at least one tubeness measure for each voxel.

In some optional embodiments of the invention, the tubular enhancement may comprise, for each voxel within the volume of the medical imaging scan data, computing at least one metric distinguishing tubular structures from other structures and computing a tubeness measure for the respective voxel based at least partly on the at least one metric.

In some optional embodiments of the invention, the tubular enhancement may comprise, for each voxel within the volume of the medical imaging scan data, computing a first metric distinguishing tubular structures from spherical structures and a second metric distinguishing tubular structures from plate-like structures, and computing a tubeness measure for the respective voxel based at least partly on the first metric, the second metric and a scan intensity value for the respective voxel.

In some optional embodiments of the invention, the method may comprise using multi-scale Hessian based tubular biliary structure enhancement.

In some optional embodiments of the invention, the volumetric medical imaging scan data may comprise imaging scan data obtained via a magnetic resonance imaging modality.

According to example embodiments of a second aspect of the present invention, there is provided an image processing system arranged to generate quantitative data for biliary tree structures from volumetric medical imaging scan data. The image processing system comprises at least one processing device arranged to perform segmentation of a volume of the medical imaging scan data to identify tubular biliary structures within the volume of the medical imaging scan data, for at least one segmented tubular biliary structure within the volume of the medical imaging scan data compute at least one set of quantitative structural parameters for at least one location along the length of the tubular biliary structure, and output quantitative biliary tree data comprising the at least one set of quantitative structural parameters for the at least one segmented tubular biliary structure.

According to example embodiments of a third aspect of the present invention, there is provided a non-transitory computer program product having stored therein executable computer program code for generating quantitative data for biliary tree structures from volumetric medical imaging scan data, the executable computer program code operable to perform the method according to the first aspect of the present invention.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION OF THE PREFERRED EMBODIMENTS

The present invention will now be described with reference to the accompanying drawings in which there is illustrated an example of a method and apparatus for generating quantitative data for biliary tree structures from volumetric medical imaging scan data. However, it will be appreciated that the present invention is not limited to the specific examples herein described and as illustrated in the accompanying drawings.

Furthermore, because the illustrated embodiments of the present invention may for the most part, be implemented using electronic components and circuits known to those skilled in the art, details will not be explained in any greater detail than that considered necessary as illustrated below, for the understanding and appreciation of the underlying concepts of the present invention and in order not to obfuscate or distract from the teachings of the present invention.

Figure 2:
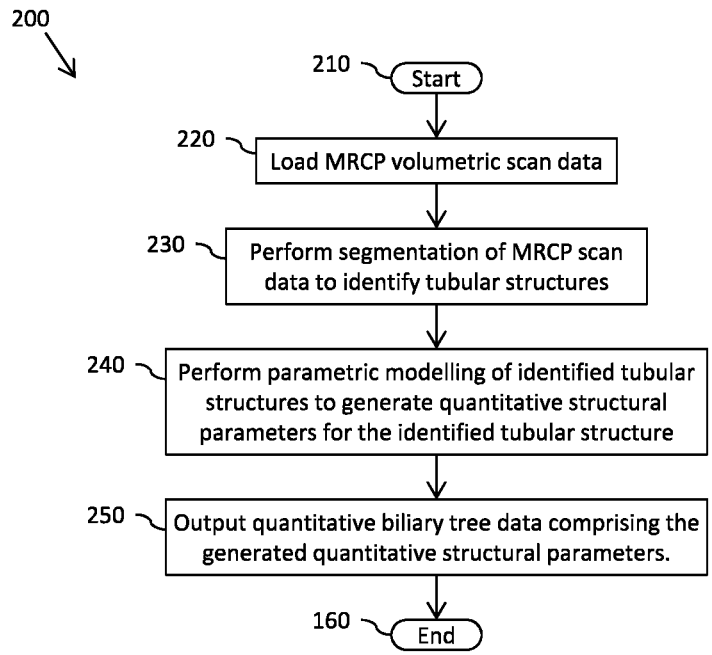
FIG. 2 illustrates a simplified flowchart of an example of at least a part of method of generating quantitative data for biliary tree structures from volumetric medical imaging scan data.

Referring now to FIG. 2, there is illustrated a simplified flowchart 200 of at least a part of method of generating quantitative data for biliary tree structures from volumetric medical imaging scan data. The method starts at 210 and moves on to 220 where volumetric scan data is loaded, the volumetric data representing a volume containing at least a part of a patient's liver. In the example illustrated in FIG. 2, the volumetric scan data comprises imaging scan data obtained via a magnetic resonance imaging modality, and in particular comprises Magnetic Resonance Cholangio-Pancreatography (MRCP) imaging scan data. Segmentation of at least one volume defined by the loaded volumetric scan data is performed, at 230, to identify tubular biliary structures within the volume. Parametric modelling of identified tubular biliary structures is then performed at 240 to generate quantitative structural parameters for the identified tubular biliary structures.

Contemplated examples of the types of quantitative structural parameters that may be generated by way of the parametric modelling include:
- one or more centre-line positions of the segmented tubular biliary structure;
- centre-line orientation of the segmented tubular biliary structure at one or more locations along the length of the segmented tubular biliary structure;
- radius values of the segmented tubular biliary structure at one or more locations along the length of the biliary structure;
- diameter values of the segmented tubular biliary structure at one or more locations along the length of the biliary structure;
- cross-sectional orientations of the segmented tubular biliary structure at one or more locations along the length of the biliary structure;
- cross-section profiles (shapes) of the segmented tubular biliary structure at one or more locations along the length of the biliary structure;
- indications of the presence of branching points for the segmented tubular biliary structure at one or more locations along the length of the biliary structure; and
- orientations of branching points for the segmented tubular biliary structure at one or more locations along the length of the biliary structure.

In particular for some example embodiments of the present invention, and as described in greater detail below, the method may comprise determining such quantitative structural parameters at a plurality of locations along the length of each identified tubular biliary structure.

Having generated the quantitative structural parameters for the identified tubular biliary structures, quantitative biliary tree data comprising the generated quantitative structural parameters is then output at 250, for example to a database or other data storage device, and the method ends at 260.

Advantageously, by generating such quantitative biliary tree data comprising the generated quantitative structural parameters from volumetric scan data obtained via, say, a magnetic resonance imaging modality, a clinician is provided with enhanced information relating to the biliary tree of a patient that enables the clinician to more accurately assess the pathology of the patient's biliary tree, and in particular to more accurately assess topological and structural features of the biliary tree such as the presence of strictures and dilatations. In this manner, embodiments of the present invention provide an improved non-invasive diagnostic technique that enables a clinician to detect liver diseases, and more generally an improved non-invasive diagnostic technique for providing a clinician with an accurate assessment of the biliary tree.

Example embodiments of the present invention will now be described in greater detail. Segmentation of medical scan images, and of digital images in general, is a well-known process of identifying objects and boundaries within an image and assigning a label to each pixel/voxel in the image such that pixels that share certain characteristics are assigned the same label. The simplest method of image segmentation is called 'thresholding', where greyscale digital image data is converted into binary image data based on a comparison of the greyscale data for each pixel/voxel to a threshold value.

However, biliary ducts are small tubes that act as a drainage system for the liver. The intrahepatic ducts typically have a diameter range of 1 mm-3 mm and the extrahepatic biliary ducts typically have a diameter range between 4 mm-8 mm. As a result, the smaller biliary ducts are often too small to be identified using such standard segmentation techniques.

Accordingly, in some example embodiments of the present invention it is proposed to perform tubular enhancement on the unprocessed medical scan data to improve the identification of tubular structures such as biliary ducts within the volumetric medical imaging scan data. Tubular enhancement aims to enhance the signal of likely tubular structures while suppressing the signal of non-tubular structures.

There are various known techniques for tubular structure enhancement. Some known techniques work at a fixed scale and use non-linear combinations of finite difference operators applied in a set of orientations. These fixed scale analysis techniques are problematic where tubular structures of a range of sizes are required to be identified, as is the case when identifying biliary ducts of varying size within a patient's liver. Various multi-scale approaches for tubular structure enhancement have been proposed, including those proposed in:

Aylward S, "Intensity ridge and widths for tubular object segmentation and description", In A. A. Amini, F. L. Bookstein, D. C. Wilson, eds., Math. Meth. In Biomedical Image Analysis 1995: 131-138;

Koller T M, et al, "Multiscale detection of curvilinear structures in 2D and 3D image data", Proceedings of Fifth International Conference on Computer Visualization 1995: 864-869;

Lorenz C, et al, "Multi-scale line segmentation with automatic estimation of width, contrast and tangential direction in 2D and 3D medical images", Lecture Notes in Computer Science 1997: 233-242 ("Lorenz");

Gradshteyn, I. S. and Ryzhik, I. M. "Hessian Determinants." § 14.314 in Tables of Integrals, Series, and Products, 6th ed. San Diego, Calif.: Academic Press, p. 1069, 2000. ("Hessian");

Sato Y, Nakajima S, Shiranga N, et al, "Three-dimensional multi-scale line filter for segmentation and visualization of curvilinear structures in medical images", Medical Image Analysis 1998; 2(2):143-168 ("Sato"); and Frangi A F, Niessen W J, Vincken K L, Viergever M A, "Multiscale vessel enhancement filtering", Medical Image Computing and Computer-Assisted Intervention (MICCAI) 1998; 1496:130-137 ("Frangi").

However, these prior art multi-scale approaches for tubular structure enhancement have proved to be unreliable in terms of achieving accurate tubular enhancement every time, due to their generic intended scope. A key clinical requirement for diagnostic techniques is the accuracy and repeatability of the techniques used.

The inventors have recognised that the reliability and accuracy of such multi-scale approaches for tubular structure enhancement may be improved by adapting them to be more application specific. In accordance with some example embodiments of the present invention, it is proposed to implement an adapted version of a Hessian based multi-scale tubular structure enhancement technique as outlined in Sato and Frangi. Accordingly, the proposed tubular structure enhancement techniques proposed in Hessian, Sato and Frangi are incorporated herein by reference.

The multi-scale approach is used to cater for biliary ducts of varying sizes within the biliary anatomy. A-priori anatomical knowledge about the size of biliary ducts may be used to adapt the tubular enhancement, and in particular may be used in choosing the size of the 3D Gaussian kernels employed within the proposed tubular structure enhancement method.

A tube is a 3D structure or 3D edge in terms of imaging. As outlined in Sato and Frangi, the process of edge enhancement (and detection) can be derived from the first-order and second-order derivative of the Gaussian. The maxima of the second-order derivative corresponds to the maxima of the original signal. Since, we are interested in a 3D Gaussian, the second-order derivatives include the double derivatives in each of the three orthogonal directions and three intermediate directional partial double derivatives.

The second-order derivatives can be expressed as a square symmetric matrix that describes all the second-order derivatives of the function. This matrix is known as the Hessian matrix. The second-order derivative of a Gaussian at a scale $\sigma$ generates a probe kernel that measures the contrast between regions inside and outside the corresponding range $(-\sigma, +\sigma)$. Eigenvalue analysis of the second-order derivatives may be used to extract the principle directions in which the local second-order structure of the image can be decomposed. The eigenvalue analysis of the Hessian matrix describes the principle modes of intensity/contrast variation. The eigenvector corresponding to the largest eigenvalue represents the direction along which the second-order derivative is maximum (maximum intensity variation), i.e. in the direction of the cross-section of the tube. Correspondingly, the eigenvector of the smallest eigenvalue represents the direction of minimum intensity variation, i.e. the direction along the length of the tube.

As described in Frangi, tube-similarity conditions and measures can be derived utilizing information about tubular geometry and eigenvalue analysis. The Eigen values ($\lambda_1$, $\lambda_2$, $\lambda_3$) are ordered in ascending order of their magnitude:

$$|\lambda_1| \leq |\lambda_2| \leq |\lambda_3| \qquad \text{Equation 1}$$

The ideal conditions that represent an ideal bright tubular structure against a dark background are:

$$|\lambda_1| \approx 0 \qquad \text{Equation 2}$$

$$|\lambda_1| \ll |\lambda_2| \qquad \text{Equation 3}$$

$$\lambda_2 \approx \lambda_3 \qquad \text{Equation 4}$$

Using the above ideal conditions, metrics can be derived to distinguish a tubular structure from other shapes. A first metric consisting of ratio $R_a$ may be given by:

$$R_a = \frac{\text{(Largest cross section area)}/\pi}{\text{(Largest axis semilength)}^2} = \frac{|\lambda_2|}{|\lambda_3|} \qquad \text{Equation 5}$$

Ratio $R_a$ distinguishes between plate-like and tubular objects. For a tubular object, this ratio attains a value close to 1, and is close to zero for a plate-like object.

A second metric consisting of ratio $R_b$ may be defined by:

$$R_b = \frac{\text{Volume}/(4\pi/3)}{\text{(Largest cross section area}/\pi)^{3/2}} = \frac{|\lambda_1|}{\sqrt{|\lambda_2 \lambda_3|}} \qquad \text{Equation 6}$$

Ratio $R_b$ distinguishes between a blob-like (spherical) object and a tubular object. This ratio attains a maximum for a spherical object, and is close to zero for a tubular object.

Note that the two ratios are geometric, and thus grey level invariant. However, the grey level information may also be a potentially discriminating factor. For example, biliary ducts typically appear very bright compared to non-biliary structures in an MRCP image. Accordingly, a third metric S may be used that takes advantage of this grey level characteristic, where S is given by:

$$S = \sqrt{\sum_{j \leq D} \lambda_j^2} \qquad \text{Equation 7}$$

An ideal tubular structure, which appears bright against dark background, should satisfy the following conditions:
(i) Small value of $R_b$;
(ii) Large value of $R_a$; and
(iii) Large value of S For a spherical, blob-like structure, one would get a high value of $R_b$. This is a useful observation, as there is often local sphericity at a branching location of the biliary tree.

The above three metrics ($R_b$, $R_a$, S) can be combined to arrive at a composite metric that measures the 'tubeness' at a particular scale a, for example:

$$T_o(\sigma) = \begin{cases} 0 & \text{if } \lambda_2 > 0 \text{ or } \lambda_3 > 0 \\ \left(1 - \exp\left(-\frac{R_A^2}{2\alpha^2}\right)\right) * \exp\left(-\frac{R_B^2}{2\beta^2}\right) * \left(1 - \exp\left(-\frac{\sigma^2}{2c^2}\right)\right) \end{cases} \qquad \text{Equation 8}$$

where α, β, c are constants that control the sensitivity of the filter.

The tubeness measure $T_o(\sigma)$ outlined in Equation 8 is computed for each voxel for each scales (σ) corresponding to varying tube sizes. The response of the filter for a particular voxel will be maximum at a scale that most closely matches the size of the tubular structure being detect. The tubeness measures for each voxel may thus be integrated over the scales to obtain a final tubeness measure as:

$$T_o = \max_{s_{min} \leq s \leq s_{max}} T_0(\sigma) \qquad \text{Equation 9}$$

The final tubeness measures for all voxels within the volumetric image, along with the corresponding eigenvalues, eigenvectors, the scale of maximal response and $R_a$ and $R_b$ values of maximal response for each voxel within the volumetric image may then be recorded. Significantly, the final tubeness measure values calculated using Equation 9 enable tubular structures such as biliary ducts, including small and faint intrahepatic ducts, to be more easily identified within the volumetric image as compared with the raw captured scan data.

Figure 3:
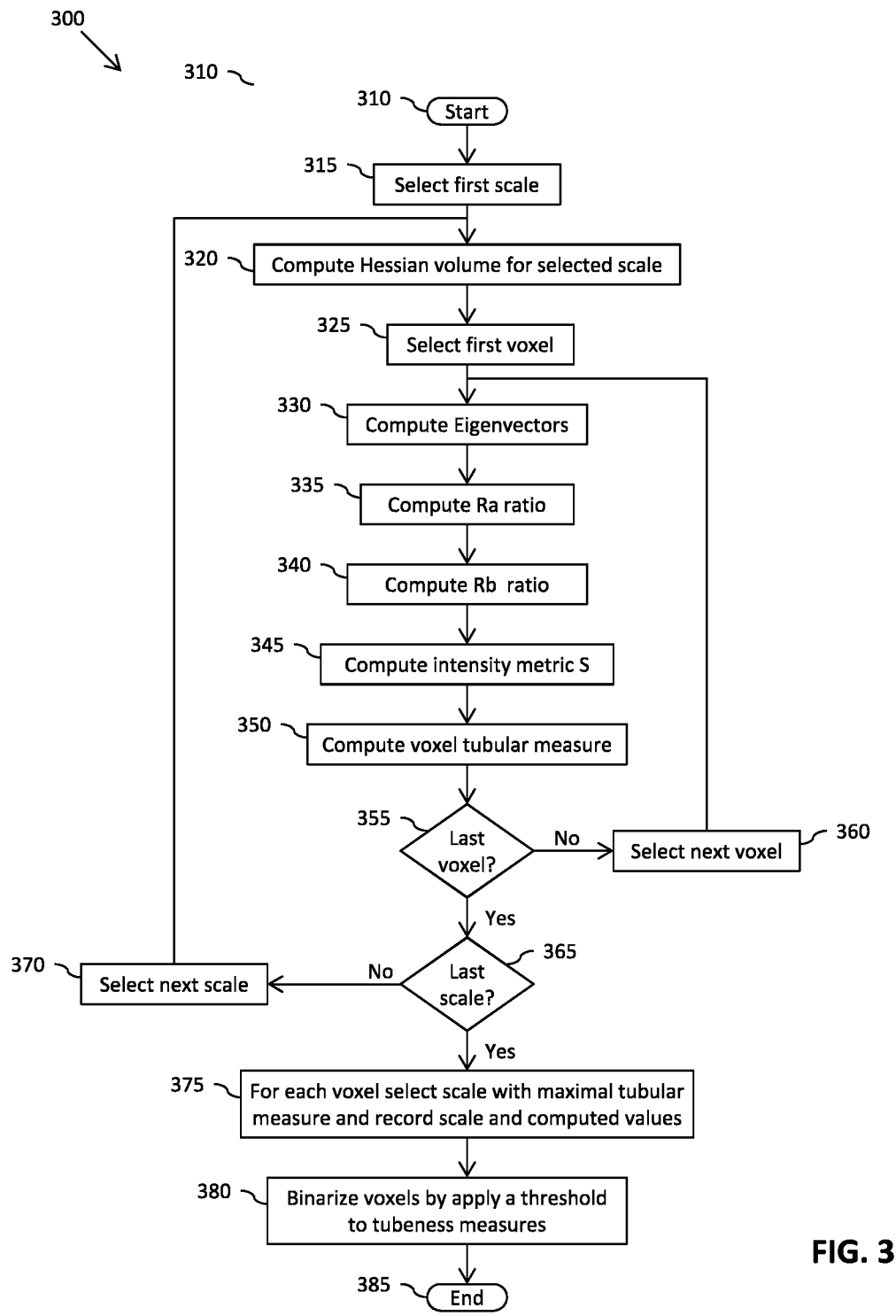
FIG. 3 illustrates a simplified flowchart of an example of performing segmentation of volumetric scan data to identify tubular biliary structures.

FIG. 3 illustrates a simplified flowchart 300 of an example of performing segmentation of volumetric scan data to identify tubular biliary structures, such as may be performed at step 230 of FIG. 2. In the example illustrated in FIG. 3, the method comprises performing tubular enhancement on the volumetric medical imaging scan data to derive a tubeness measure for each voxel within the volumetric medical imaging scan data, for example as described above, and performing segmentation of the medical imaging scan data based on the tubeness measure for each voxel.

The method of FIG. 3 starts at 310 and moves on to 315 where a first scale a, for example from a predefined set of scales representative of typical biliary duct widths, is selected. In the illustrated example, the Hessian volume for the selected scale is then computed at 320, whereby the Hessian matrix of second-order Gaussian derivatives for each voxel within the volume to be segmented is computed, the computed Hessian matrices forming the Hessian volume.

A first voxel within the Hessian volume is then selected at 325, and the Eigenvectors for the second-order Gaussian derivatives within the Hessian matrix for the selected voxel are computed. Metrics distinguishing tubular structures from other shaped structures are then computed for the selected voxel. In particular for the illustrated example, a first metric $R_a$ distinguishing between plate-like and tubular structures is computed at 335, for example by way of Equation 5 above, and a second metric $R_b$ distinguishing between blob-like (spherical) and tubular structures is computed at 340, for example by way of Equation 6 above. In the illustrated example, a third metric S representative of signal intensity (grey level) for the selected voxel is then computed at 345, for example by way of Equation 7 above. A tubeness measure $T_o(\sigma)$ for the selected scale a and selected voxel is then computed, at 350, using the computed metrics, for example using Equation 8.

It is then determined whether the selected voxel is the last voxel, i.e. that a tubeness measure for the selected scale a has been computed for all voxels within the volume, at 355. If it is determined that the currently selected voxel is not the last voxel, the method moves on to 360 and the next voxel in the volume is selected and the method loops back to 330. In this manner, the method loops until a tubeness measure $T_o(\sigma)$ for the selected scale a is computed for each voxel within the volume.

Once a tubeness measure $T_o(\sigma)$ has been computed for all voxels in the volume for the selected scale σ, the method moves on to 365 where it is determined whether the selected scale σ is the last scales, i.e. that tubeness measures have been computed for all scales within the pre-defined set of scales. If it is determined that the currently selected scale is not the last scale, the method moves on to 370 and the next scale in the set is selected and the method loops back to 320. In this manner, the method loops until tubeness measures for all scales are computed.

Once tubeness measures for all scales have been computed, the method moves on to 375 where for each voxel in the volume a final tubeness measure is derived from the set of tubeness measures computed for the set of scales, for example using Equation 9 above where the maximal tubeness measure from the set of tubeness measures for a voxel is selected as the final tubeness measure for that voxel. The derived final tubeness measure, along with the corresponding eigenvalues, eigenvectors, the scale of maximal response and $R_a$ and $R_b$ values of maximal response for each voxel within the volumetric image are then be recorded.

Having derived the final tubeness measure for each voxel within the volume, segmentation is performed based on the final tubeness measures, at 380. In the example illustrated in FIG. 3, the segmentation of the volumetric image data is performed by applying a threshold to the final tubeness measures to generate binary (i.e. '1' or '0') values for the voxels within the volume indicating which voxels correspond to tubular structures within the image data. The method of FIG. 3 then ends, at 385.

Referring back to FIG. 2, having performed segmentation of the volumetric scan data at 230, parametric modelling of the identified tubular structures is then performed to generate quantitative structural parameters for the identified tubular structures. In accordance with some example embodiments of the present invention, such parametric modelling comprises computing a hierarchical parametric representation of the biliary tree, where an individual biliary duct can be selected and metrics computed on it. In this manner, individual biliary ducts may be identified and quantified.

Figure 4:
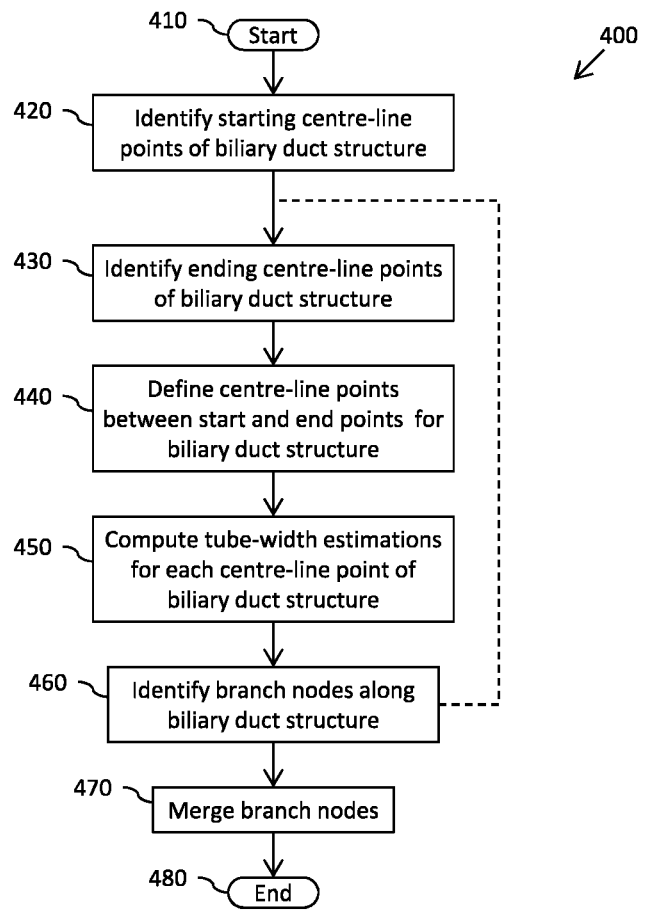
FIG. 4 illustrates a simplified flowchart of an example of a parametric modelling process.

FIG. 4 illustrates a simplified flowchart 400 of an example of such a parametric modelling process. The method starts at 410 and moves on to 420 where a starting centre-line points of a biliary duct structure (i.e. the axially central point at the start of the biliary duct) within the segmented volume to be modelled are identified. For example, in the case of a major biliary duct, such as the common hepatic duct, the starting centre-line point may be identified based on user input. Conversely, in some examples branching points identified along the length of a biliary duct structure (as described in greater detail below) may be used as the starting centre-line points for 'child' biliary duct structures. Having identified the starting centre-line point, the ending centre-line point of a biliary structure is then determined, at 430, for example by finding a point within the segmented volume that has a 'medialness' value closest to that of starting centre-line point and that maximizes the Euclidean distance from the starting centre-line point.

Figure 5:
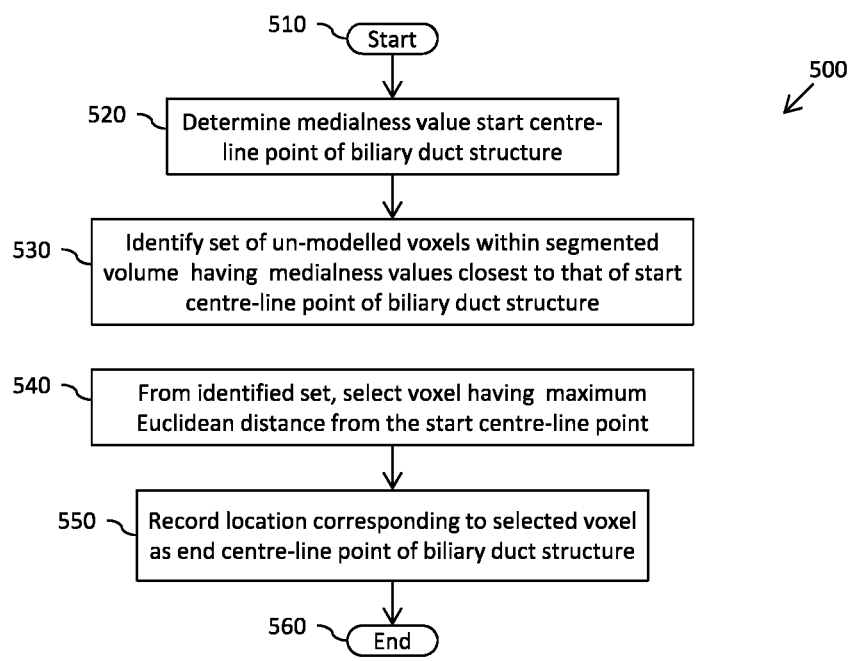
FIG. 5 illustrates a simplified flowchart of an example of a method of finding an ending centre-line point of a biliary structure.

FIG. 5 illustrates a simplified flowchart 500 of an example of such a method of finding an ending centre-line point of a biliary structure. The method starts at 510 and moves on to 520 where in the illustrated example a medialness value for the starting centre-line point is determined. For example, a medialness map may be generated for the segmented volume. In some examples, a Gradient Vector Flow (GVF) field based computation may be performed for generating the medialness map as outlined in Bauer C, Bischof H, "Extracting curve skeletons from gray value images for virtual endoscopy", Lecture Notes in Computer Science 2008; 5128:393-402, which is incorporated herein by reference.

Having determined a medialness value for the starting centre-line point, the method moves on to 530 where a set of un-modelled voxels within the segmented volume (i.e. those voxels labelled as corresponding to tubular structures during segmentation but located within regions of the segmented volume yet to be parametrically modelled) having medialness values closest to the medialness value of the starting centre-line point are identified. For example, the set of un-modelled voxels having medialness values within maximum deviation from the medialness value of the starting centre-line point may be identified. Since the medialness value for a voxel is indicative of not only the probability of the voxel corresponding to a centre-line of a biliary structure, but also of the cross-sectional properties (e.g. size) of the respective biliary structure, voxels corresponding to the centre-line of a biliary structure are likely to have similar medialness values. Accordingly, by identifying the set of voxels having medialness values closest to the medialness value of the starting centre-line point, the identified set of voxels are likely to correspond to the centre-line points for the same biliary structure to which the start centre-point relates.

From the identified set of un-modelled voxels, the voxel having the maximum Euclidean distance from the starting centre-line points is selected at 540, on the assumption that the ending centre-line point will be the centre-line point within the biliary structure located furthest away from the starting centre-line point. The location corresponding to the selected voxel is then recorded as the ending centre-line point of the biliary duct structure at 550, and the method ends at 560.

Referring back to FIG. 4, having identified the start and ending centre-line points of the biliary duct structure, the method moves on to 440 where centre-line points for the biliary duct structure between the starting and ending centre-line points are defined, the objective being to find a center-line skeleton of the biliary duct. For example, centre-line points for the biliary duct structure may be defined by, incrementally starting from the starting centre-line point, determining successive centre-line points for the biliary structure until the ending centre-line point is reached.

Figure 6:
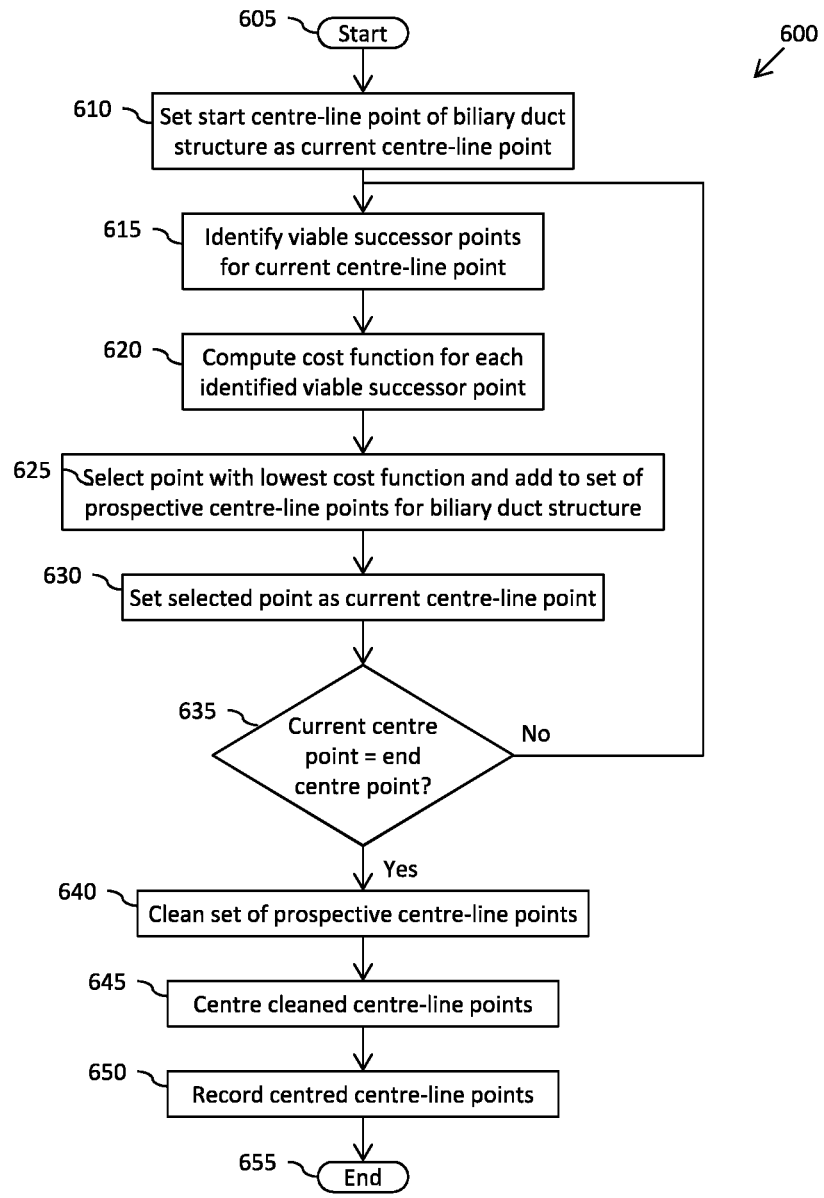
FIG. 6 illustrates a simplified flowchart of a method of incrementally defining centre-line points for a biliary duct structure.

FIG. 6 illustrates a simplified flowchart 600 of such a method of incrementally defining centre-line points for a biliary duct structure. The method of FIG. 6 is based on a weighted search algorithm for finding an optimal path that connects the starting centre-line point and the ending centre-line point, where the weight indicates the 'cost' of moving from one point to the next. The method starts at 605 and moves on to 610 where the starting centre-line point for the biliary duct structure is set as the current centre-point. Viable successor points for the current centre-line point are then identified at 615. For example, only those points connected to (e.g. directly adjacent to) the current centre-line point and that satisfy defined viability criteria may be deemed viable successor points. Thus, viable successor points may be limited to the 26 points immediately surrounding the current centre-line point within the 3-dimensional (volumetric) space. From the 26 points immediately surrounding the current centre-line point, the viable successor points may be identified as those that satisfy the criteria of, for example, one or more of:

(i) is part of the segmentation (i.e. corresponds to an identified tubular structure within the segmented volume);

(ii) has not already been recorded as a candidate centre-line;

(iii) satisfies a distance map threshold criteria or Laplacian of Gaussian threshold criteria;

(iv) is in a viable orientation; etc.

With regard to a distance map threshold criteria, a distance map may be computed from the segmented volume, wherein each voxel value represents the distance of the voxel from the surface of an identified tubular structure. Voxels lying within identified tubular structures are assigned negative values, whilst voxels lying outside identified tubular structures are assigned positive values. Thus a voxel lying close to the centre line of an identified tubular structure would be assigned a high negative value, and as one moves towards the surface the voxel values tend towards zero. As one moves outside of the tubular structure, the value will turn positive and increase as one moves away from the surface of the tubular structure.

With regard to a viable orientation for a candidate successor centre-line point, a predictive orientation vector may be computed from, say, four centre-line points preceding the current centre-line point to the current-line point. In this manner, the predictive orientation vector is representative of the historic orientation of the centre-line for the biliary duct structure, and serves as a good predictor of the next centre-line point since despite having varying curvature along the length of a biliary duct structure, a short section of the biliary duct structure may be considered as piece-wise linear. A corresponding candidate orientation vector may be computed from the current centre-line point to the candidate successor centre-line point. The candidate successor centre-line point may then be deemed to satisfy the viable orientation if, for example, the vector dot product of the predictive orientation vector and the candidate orientation vector is positive.

In some example embodiments, if too few (e.g. none) or too many viable successor centre-line points are identified, adaptive thresholds may be used for constraining or relaxing the search criteria. For example, for the above example criteria the distance map threshold criteria and/or Laplacian of Gaussian threshold criteria may be constrained or relaxed. For instance, starting with stringent distance map threshold criteria, if no viable successor centre-line points found, iteratively relax distance map threshold criteria and re-evaluate candidate successor centre-line points. If distance map threshold reaches a positive value without identifying any viable successor centre-line points, switch to Laplacian of Gaussian threshold criteria instead of distance map threshold criteria. Starting with stringent Laplacian of Gaussian threshold criteria, evaluate candidate successor centre-line points. If no viable successor points found, iteratively reduce scale of Laplacian of Gaussian and re-evaluate candidate successor centre-line points. If no viable successor centre-line points found after Laplacian of Gaussian scale has reached is minimum scale, declare failure to find successor centre-line point.

Referring back to FIG. 6, having identified viable successor centre-line points, the method moves on to 620 where cost functions are computed for the viable successor centre-line points. For example, the cost function for a viable successor centre-line point may be computed based on one or more of the following:
(i) Start point cost ($SP_{dist}$): the distance between the viable successor centre-line point and the starting centre-point;
(ii) End point cost ($EP_{dist}$): the distance between the viable successor centre-line point and the ending centre-point;
(iii) Tubeness gain ($T_o$): the tubeness measure $T_o$ for the voxel of the viable successor centre-line point (e.g. see Equation 9);
(iv) Medialness gain ($M_o$): the medialness value for the voxel of the viable successor centre-line point;
(v) Adhering to predictive orientation cost (APO): 1—vector dot product of the predictive orientation vector and the candidate orientation vector;
(vi) $R_b$ cost ($R_b$): $R_b$ metric value for the voxel of the viable successor centre-line point; and
(vii) Laplacian of Gaussian (LOG) cost: LOG value for the viable successor centre-line point.

Referring back to FIG. 6, having computed the cost functions for the identified viable successor centre-line points, the viable successor centre-line point with the lowest computed cost is selected and added to a set of prospective centre-line points for the biliary duct structure at 625. The selected point is then set as the current centre-line point, at 630. It is then determined whether the (new) current centre-line point is the ending centre-line point for the biliary duct structure. If the current centre-line point is not the ending centre-line point for the biliary duct structure, the method loops back to 615. However, if the current centre-line point is the ending centre-line point for the biliary duct structure, the method of FIG. 6 moves on to 640 where in the illustrated example the set of prospective centre-line points for the biliary duct structure is 'cleaned'.

The objective of this step is to clean the set of prospective centre-line points of possible 'near-cycles'. For example, if there is a direct connectivity of a current recorded centre-line point to a recorded centre-line point 'n' points upstream, then the presence of 'near-cycle' is quite likely, in which case the spurious recorded centre-line points between the current recorded centre-line point and the $n^{th}$ centre-line point upstream need to be removed. This is achieved by traversing the recorded centre-line points node by node. For example, for each node (recorded centre-line point):
(i) look 4 nodes ahead:
a. compute the distance between the 4th node and the current node;
b. if the distance is less than or equal to 1.717 voxels (square root of 3—increment of 1 voxel in each dimension and still connected to the node), remove nodes between the $4^{th}$ node and the current node.
(ii) look 3 nodes ahead:
a. compute the distance between the 4th node and the current node;
b. if the distance is less than or equal to 1.717 voxels, remove nodes between the $3^{rd}$ node and the current node.
(iii) look 2 nodes ahead:
a. compute the distance between the $2^{nd}$ node and the current node;
b. if the distance is less than or equal to 1.717 voxels, remove nodes between the $2^{nd}$ node and the current node.

Referring back to FIG. 6, having cleaned the set of prospective centre-line points for the biliary duct structure, the method of FIG. 6 moves on to 645 where in the illustrated example the cleaned centre-line points are centred, and the centred centre-line points recorded at 650.

The centring of the cleaned centre-line points is performed to ensure that the recorded centre-line defined by the (cleaned) centre-line points found is accurately centred with respect to the segmented tubular biliary structure. For example, this may be achieved by traversing along the recorded centre-line point by point and for each recorded centre-line point:
(i) make the current centre-line point the 'anchor node';
(ii) make the subsequent centre-line point the 'optimizing node';
(iii) compute the vector from the anchor node to optimizing node;
(iv) in the neighbourhood of the optimizing node, search for a 'better' candidate location that:
a. has higher Medialness response (more likely to be central voxel);
b. the vector from anchor node to this location is in same general direction as the vector from the anchor node to optimizing node (preserve general direction); and
c. is connected to the optimizing node's following connecting node (preserve connectivity), and (v) if these criteria are met, replace the optimizing node with the better candidate location.

Referring back to FIG. 6, having centred and recorded the centre-line points, the method illustrated in FIG. 6 ends, at 655.

The flow chart of FIG. 6 accurately describes how a single 'branch' of the biliary tree is constructed. However, in practice, there are situations where multiple possible paths for the branch are constructed. In that case, only when the 'end centre' point has been reached, is the overall 'optimal path' determined.

Referring back to FIG. 4, having defined the centre-line points for the biliary duct structure between the start and ending centre-line points, the method moves on to 450 where tube-width estimations are computed along the length of the biliary duct structure, for example corresponding to each centre-line point defined at step 440.

In some example embodiments, a tube-width estimate corresponding to a centre-line point for the biliary duct structure may be computed as follows. The scale σ of maximal response for the voxel corresponding to the centre-line point, obtained when performing tubular enhancement on the medical scan data (see FIG. 3), may be used to define a tube-width search radius. In some examples, the tube-width estimation for each location may be computed by determining a cross-sectional orientation of the biliary duct structure at the respective location and determining a tube-width estimation for the biliary duct structure in the determined cross-sectional orientation. For example, the Eigenvectors for the second-order Gaussian derivatives within the Hessian matrix for the voxel corresponding to the centre-line point, computed when performing tubular enhancement on the medical scan data, may be used to determine an orientation of a cross-section search area having a radius equal to the tube-width search radius. A search is then performed for non-zero voxels of the segmented volume (i.e. voxels labelled as forming part of a tubular structure) within the cross-section search area. A circular cross-section area model $\pi \ast r^2$ is then set equal to the number of non-zero voxels found and the radius r computed. The tube-width for the centre-line point may then be estimated at $2 \ast r$.

Having computed the tube-width estimates for each centre-line point of the biliary duct structure, the method of FIG. 4 moves on to 460 where branch nodes along the biliary duct structure are identified.

Figure 7:
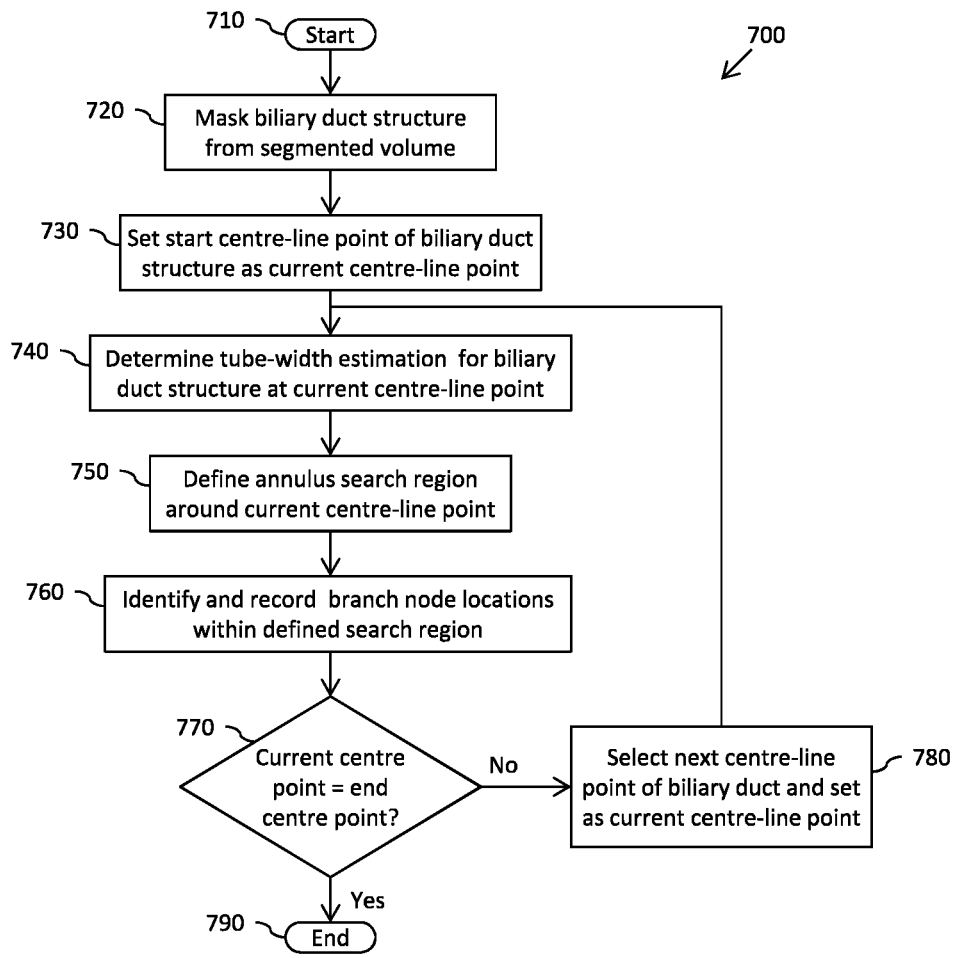
FIG. 7 illustrates a simplified flowchart of an example of a method for identifying branch nodes along a biliary duct structure.

FIG. 7 illustrates a simplified flowchart 700 of an example of a method for identifying branch nodes along a biliary duct structure, such as may be implanted at step 460 of FIG. 4. The method of FIG. 7 starts at 710 and moves on to 720 where the current biliary duct structure is masked from the segmented volume. Masking the current biliary duct structure in the manner facilitates the detection of further biliary duct structures branching off from the current biliary duct structure. According to some example embodiments of the present invention, the masking of the current biliary duct structure may be achieved by performing the following for each centre-line point of the biliary duct structure:
(i) compute the centre-line orientation vector, connecting current centre-line point with next centre-line point;
(ii) form a search neighbourhood with radius equal to half of the estimated tube-width at the current centre-line point;
(iii) for each voxel in the search neighbourhood (candidate location):
a. compute the vector from the current centre-line point to the candidate voxel;
b. compute vector dot product with centre-line orientation vector;
c. if the computed dot product is close to zero (i.e. lies in orthogonal plane to centre-line orientation vector), set the candidate voxel in the (binary) segmented volume to zero (mask.

Referring back to FIG. 7, having masked the current biliary duct structure from the segmented volume, the method moves on to 730 where the starting centre-line point for the current biliary duct structure is set as the current centre-line point. The tube-width estimation for the current centre-line point is determined at 740, for example as previously computed at step 440 of the method of FIG. 4. An annulus (ring-shaped) search region is then defined around the current centre-line point based on the tube-width estimation therefor, at 750. For example, the annulus search region may be defined by an inner radius equal to the tube-width estimation and an outer radius equal to the tube-width estimation +Δ (Δ being a predefined search region width). The Eigenvectors for the second-order Gaussian derivatives within the Hessian matrix for the voxel corresponding to the current centre-line point, computed when performing tubular enhancement on the medical scan data, may be used to determine an orientation of the annulus search region. Branch node locations are then identified within the search region and recorded at 760. For example, non-zero voxels of the (masked) segmented volume within the annulus search region may be used to identify branch points. In this manner, points corresponding to identified tubular structures within the segmented volume located within a region A deep externally along the length of the (masked out) current biliary duct structure are identified and recorded.

Having identified and recorded the branch nodes for the current centre-line point, the method moves on to 770, where it is determined, whether the current centre-line point is the ending centre-line point of the current biliary duct structure. If it is determined that the current centre-line point is not the ending centre-line point for the current biliary duct structure, the method moves on to 780 where the next centre-line point of the current biliary duct structure is set as the current centre-line point, and the method loops back to 740. In this manner, the method iteratively identifies and records branch nodes for all centre-line points of the current biliary duct structure.

Having identified and recorded branch nodes for all centre-line points of the current biliary duct structure, the method ends at 790.

Significantly, by identifying branch nodes in this manner, the starting centre-line points for child biliary duct structures may be identified and recorded. These may then be used to find the ending centre-line points for the respective child biliary duct structures, for example by way of the method illustrated in FIG. 5. The starting and ending centre-line points for the child biliary duct structures may then be used to find the remaining centre-line points for the respective child biliary duct structures, for example by way of the method of FIG. 6, and tube-width estimates for each centre-line point of the child biliary duct structures computed, for example as described above. Branch nodes for the child biliary duct structures may then be identified, for example by way of the method of FIG. 7 to identify branch nodes for grandchild biliary duct structures.

Accordingly, and referring back to FIG. 4, having identified branch nodes for the current biliary duct structure, the identified branch nodes may be used as starting centre line points for 'child' biliary duct structures, and the method may loop back to 430 for each identified branch node to such a performing parametric modelling of the respective child biliary duct structures, such as indicated by the dashed line in FIG. 4.

Having performed parametric modelling of identified biliary duct structures, the method illustrated in FIG. 4 moves on to 470 where centre-lines of child biliary duct structures are merged back to centre-line points within their respective parent biliary duct structures from which they branch. In this manner, a centre-line 'skeleton' structure for the biliary tree structure may be formed. For example, for each identified branch (chiled) biliary duct structure:
- compute a local orientation vector connecting a first (closest to parent biliary duct structure) centre-line point of the branch biliary duct structure to an $n^{th}$ closest centre-line point of the branch biliary duct structure;
- identify centre-line point of parent biliary duct structure closest to first centre-line point of branch biliary duct structure;
- define set of parent centre-line points comprising the identified closest centre-line point of the parent biliary duct structure and, say, 10 centre-line points upstream and downstream of the closest centre-line point;
- compute branching orientation vectors connecting each of the set of parent centre-line points to the first centre-line point of the branch biliary duct structure; and
- select as starting centre-line point of the branch biliary duct structure the centre-line point of the parent biliary duct structure for which the vector dot product between the local orientation vector and the respective branching orientation vector yields the highest value.

Having merged all the branch nodes back to centre-line points of the parent biliary duct structure, the method of FIG. 4 ends, at 480.

Accordingly, a recursive process may be implemented whereby a full biliary tree structure may be parametrically modelled starting from the hepatic duct using the various methods hereinbefore described and as illustrated in the accompanying drawings, whereby a complete hierarchical parametric model of the biliary tree may be generated comprising:
1. a defined skeleton (centre-line) for each individual biliary duct structure;
2. tube-width estimate on each location (centre-line point) of each biliary duct structure skeleton;
3. parent-child relationship between individual biliary duct structures;
4. the locations and orientations of branch points on each biliary duct structure skeleton.

Having generated such a hierarchical parametric model of the biliary tree comprising quantitative biliary tree data, topological metrics may be computed for individual biliary ducts. For example, it is contemplated that detection and quantification of patterns of change within the biliary tree that indicate particular structural characteristics such as strictures, dilatations and beading, may be performed based on the obtained quantitative biliary tree data, and in particular on tube-width estimations.

Figure 8:
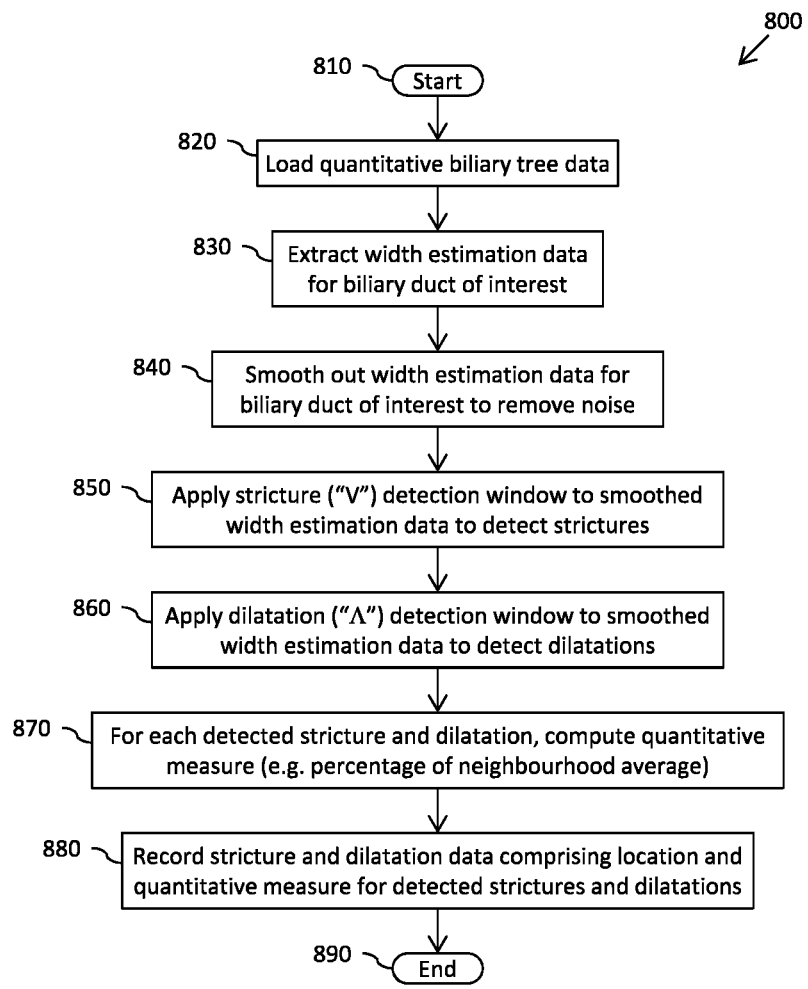
FIG. 8 illustrates a simplified flowchart of an example of a method of detecting and quantifying strictures and dilatations within a biliary duct structure.

FIG. 8 illustrates a simplified flowchart 800 of an example of a method of detecting and quantifying patterns of change indicative of strictures and dilatations within a biliary duct structure. The method of FIG. 8 starts at 810 and moves on to 820 where the quantitative biliary tree data is loaded. Tube-width estimations for a biliary duct of interest are extracted from the quantitative biliary tree data at 830. In the illustrated example the extracted tube-width estimations are smoothed out at 840 to remove noise from the tube-width estimation data that might give rise to false detections. For example, a Gaussian kernel may be applied to the tube-width estimations with a sigma of, say, 1.

Having smoothed out the tube-width estimation data, the method moves on to 850 where in the illustrated example a stricture ("V") detection window is applied to the smoothed tube-width estimation data to detect a pattern of change within the tube-width data indicative of strictures within the biliary duct of interest. For example, for any point $P_k$ along the length of the biliary duct having estimated tube-width $W_k$, a stricture is detected if the following condition is true:

$$W_{k-2} > W_{k-1} > W_k < W_{k+1} < W_{k+2} \qquad \text{Equation 10}$$

Next, a dilatation ("Λ") detection window is applied to the smoothed tube-width estimation data to detect a pattern of change within the tube-width data indicative of dilatations within the biliary duct of interest. For example, for any point $P_k$ along the length of the biliary duct having estimated tube-width $W_k$, a dilatation is detected if the following condition is true:

$$W_{k-2} < W_{k-1} < W_k > W_{k+1} > W_{k+2} \qquad \text{Equation 11}$$

Beading may also be detected, for example based on detected sequences of strictures and dilatations. Detected patterns of change within the tube-width data indicative of strictures and dilatations are then quantified, at 870, by computing a quantitative measure for detected stricture and dilatation. For example, for each detected stricture/dilatation point $P_k$, first the average width W_avg of the neighbourhood is computed as:

$$W_{avg} = \frac{(W_{k-2} + W_{k+2})}{2.0} \qquad \text{Equation 12}$$

For each detected stricture, a percentage of stricturing is computed as:

$$\text{Stricturing percentage} = 100*(W_{avg} - W_k)/W_{avg} \qquad \text{Equation 13}$$

For each detected dilatation, a percentage of dilatation is computed as:

$$\text{Dilatation percentage} = 100*(W_k - W_{avg})/W \qquad \text{Equation 14}$$

The stricture and dilatation data comprising the location and quantitative measure for each detected stricture and dilatation is then recorded at 880, and the method ends, at 890.

Figure 1:
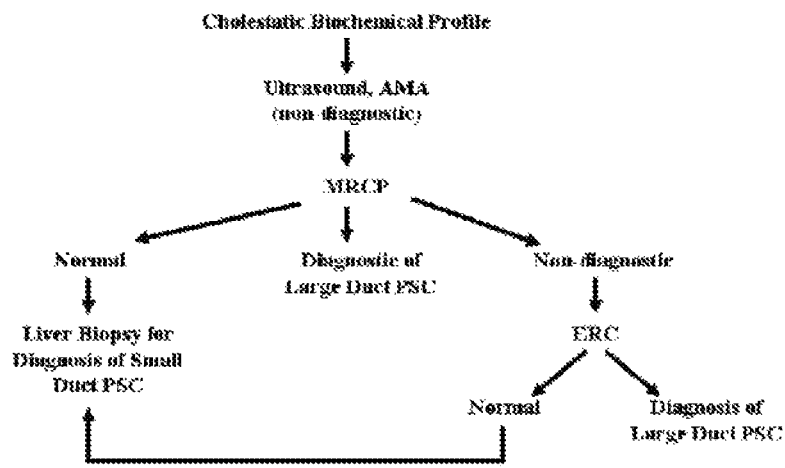
FIG. 1 illustrates the recommendations for diagnosing Primary Sclerosing Cholangitis (PSC) as documented in the American Association for the Study of Liver Diseases (AASLD) practice guidelines
Figure 9:
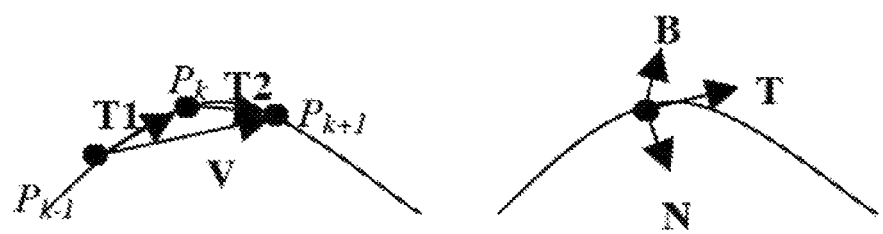
FIG. 9 illustrates an example of a Frenet-Serret frame being used to detect an inflection point.

Other topological metrics may also be computed from the quantitative biliary tree data. For example, it is contemplated that one or more of the following topological tortuosity metrics may be computed:
(i) Distance metric (DM): the ratio between the actual centre-line length (moving from centre-line point to centre-line point) and the linear distance between the starting centre-line point and ending centre-line point.
(ii) Inflection count metric (ICM): for a 3D curve, an inflection point is defined as a locus that exhibits minimum of total curvature. For detecting an inflection point, a Frenet-Serret frame may be implemented, as illustrated in FIG. 9, comprising The tangent (T), normal (N) and binormal (B) unit vectors where:
 a. T is the unit vector tangent to the curve, pointing in the direction of motion;
 b. N is the normal unit vector, the derivative of T with respect to the arc-length parameter of the curve, divided by its length; and c. B is the binormal unit vector, the cross product of T and N.

(iii) Sum of angles metric (SOAM): computed by integrating the total curvature along the curve and normalizing it by path length.

For the inflection count metric, the decomposition computation may be performed as follows. The velocity vector V at a point $P_k$ can be approximated by the vector between points $P_{k-1}$ and $P_{k+1}$. The acceleration vector A at point $P_k$ is given by:

$$A = T2 - T1 \qquad \text{Equation 15}$$

The Frenet tanget axis T is a normalized velocity vector, given by:

$$T = V/|V| \qquad \text{Equation 16}$$

The Frenet normal axis N is a normalized vector given by:

$$N = V \times A \times V/|V \times A \times V| \qquad \text{Equation 17}$$

The Frenet binormal axis B, is a normalized vector given by:

$$B = T \times N \qquad \text{Equation 18}$$

In terms of Frenet-frame decomposition, an inflection point is defined where the Normal (N) and Binormal (B) axes change orientation by close to 180 degrees as the frame passes through the curve. As a result, one can search for a 3D inflection point by identifying large local maxima of dot product:

$$\Delta N \cdot \Delta N \qquad \text{Equation 19}$$

where $\Delta N$ represents the difference of the normal axes associated with points $P_k$ and $P_{k-1}$. So at the inflection point, the length of $\Delta N$ is close to 2 units as unit vector N rotates by 180 degrees. Therefore, passage through an inflection point produces $\Delta N \cdot \Delta N$ approximately equal to 4.0 whereas values at other locations are in the range of $10^{-2}$ to $10^{-8}$. Thus one can term a point on the curve as an inflection point if $\Delta N \cdot \Delta N > 1.0$.

The Inflection Count Metric ICM may thus be defined as:

$$ICM = DM \ast \text{number of inflection points} \qquad \text{Equation 20}$$

The computation for the Sum of angles metric may be as follows. For any point $P_k$ the vectors T1, T2 and T3 are defined as:

$$T1 = P_k - P_{k-1}$$

$$T2 = P_{k+1} - P_k$$

$$T3 = P_{k+2} - P_{k+1}$$

The in-plane curvature can be estimated by using vectors T1 and T2, the in-plane angle ($IP^k$) at point $P_k$ is given by:

$$IP_k = \cos^{-1}\left(\left(\frac{T1}{|T1|}\right) \cdot \left(\frac{T2}{|T2|}\right)\right) \qquad \text{Equation 21}$$

The torsion at point $P_k$ is represented by the angle between the osculating plane whose surface normal is normalized cross product of vectors T1 and T2, and the surface normal of the subsequent plane. Just as the Frenet Normal and Binormal axes reverse direction as they cross an inflection point, the normals of two successive osculating planes will point in opposite directions when $P_k$ and $P_k+1$ lie on opposite sides of the inflection points. The torsional angle ($TP_k$) at point $P_k$ is given by:

$$TP_k = \cos^{-1}((T1 \times T2/|T1 \times T2|) \cdot (T2 \times T3)/(|T2 \times T3|)) \qquad \text{Equation 22}$$

The total angle ($CP_k$) at point $P_k$ is given by:

$$CP_k = \sqrt{(IP_k \times IP_k) + (TP_k \times TP_k)} \qquad \text{Equation 23}$$

The sum of angles metric calculates the total tortuosity of the curve as:

$$SOAM = (\Sigma_{k=1}^{n-3} CP_k)/(\Sigma_{k=1}^{n-1} |P_k - P_{k-1}|) \qquad \text{Equation 24}$$

Each of the three topological metrics (DM, ICM, SOAM) has its uses. ICM and SOAM are capable of distinguishing between sinusoidal like curves of varying frequencies. For coil-like curves, SOAM is able to distinguish between coils of varying frequencies. For curves of varying amplitudes DM and ICM can effectively distinguish. Individual biliary ducts may be assigned a tortuosity value using the three metrics.

In accordance with some example embodiments of the present invention, the quantitative biliary tree data comprising the generated quantitative structural parameters may be used in conjunction with data derived from other medical imaging scan data for the patient, for example obtained by way of different imaging modalities. For example, in magnetic resonance imaging, the accurate measurement of T1 relaxation time (time for recovery of longitudinal magnetization) is of particular interest as it is known to aid in tissue characterization and disease detection. In particular, iron-correct T1 values have been demonstrated to correlate extremely well with the inflammation and fibrosis in liver, as described in Banerjee R, Pavlides M, Tunnicliffe E, et al, "Multiparametric magnetic resonance for non-invasive diagnosis of liver disease", Hepatology 2014; 60:69-77, which is incorporated herein by reference.

Biliary strictures (a marker of PSC) are a result of progressive and chronic injury to small, medium and large biliary ducts with inflammatory and obliterative concentric periductal fibrosis (so-called onion skinning). Early stage PSC is believed to be marked by increased inflammatory and fibrotic response around the biliary ducts. Accordingly, an ability to detect inflammation and fibrosis around biliary ducts would provide an extremely powerful tool for detecting early stage PSC.

Figure 10:
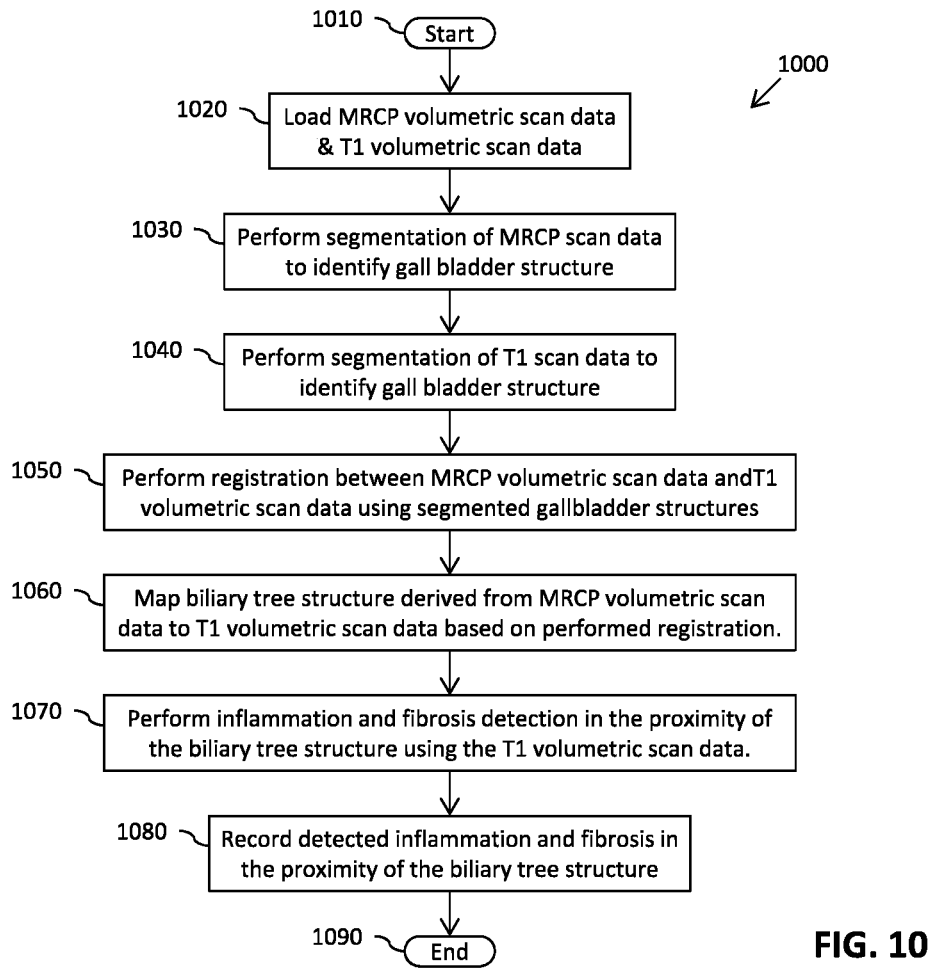
FIG. 10 illustrates a simplified flowchart of an example of a method of detecting inflammation and fibrosis in the proximity of biliary structures utilising quantitative biliary tree data comprising quantitative structural parameters.

FIG. 10 illustrates a simplified flowchart 1000 of an example of a method of detecting inflammation and fibrosis in the proximity of biliary structures utilising quantitative biliary tree data comprising quantitative structural parameters, such as generated by way of the various methods hereinbefore described. The method starts at 1010 and moves on to 1020 where MRCP volumetric scan data and T1 volumetric scan data are loaded, each of the MRCP and T1 volumetric scan data representing a volume containing a patient's liver and gallbladder. The MRCP volumetric scan data includes (or is otherwise associated with) quantitative biliary tree data comprising quantitative structural parameters defining a biliary tree structure derived from the MRCP data.

The gallbladder is shaped like a tapered sac, almost pear-shaped, with the open end opening into the biliary tree. Anatomically, the gallbladder is divided into three sections: the fundus, body, and neck: The fundus is a rounded end that faces the front of the body; the body is in contact with the liver, lying in the gallbladder fossa, a depression at the bottom of the liver; the neck tapers and is continuous with the cystic duct, part of the biliary tree. Significantly, the gallbladder is the is clearly visible in both MRCP data and T1 data. Identification/segmentation of the gallbladder in both MRCP and T1 serves as an anatomical landmark for performing registration of the T1 volume and the MRCP volume.

Accordingly, segmentation of the MRCP data is then performed at 1030 to identify the gallbladder structure within the MRCP volumetric scan data. Similarly, segmentation of the T1 data is performed at 1040 to identify the gallbladder structure within the T1 volumetric scan data. Registration is then performed between the MRCP volumetric scan data and T1 volumetric scan data using the segmented gallbladder structures to 'guide' the registration process, at 1050. In this manner, by using the segmented gallbladder structures, a reliable and accurate registration between the MRCP volumetric scan data and the T1 volumetric scan data may be achieved. Having registered the MRCP volumetric scan data with the T1 volumetric scan data, the biliary tree structure derived from the MRCP volumetric scan data is mapped to the T1 volumetric scan data based on the registration between the MRCP volumetric scan data and the T1 volumetric scan data, at 1060. Inflammation and fibrosis detection is then performed in the proximity of the biliary tree structure using the T1 volumetric scan data, at 1070, and detected strictures and dilatations in the proximity of the biliary tree structure are recorded at 1080. The method then ends at 1090.

Figure 11:
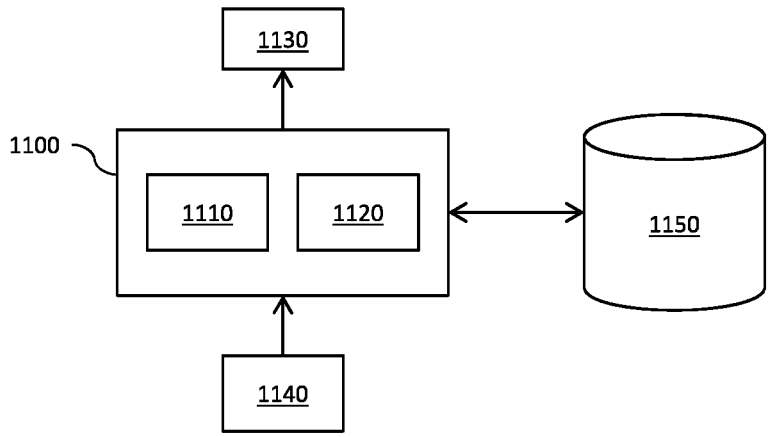
FIG. 11 illustrates a simplified block diagram of an example of an image processing system.

FIG. 11 illustrates a simplified block diagram of an example of an image processing system 1100 that may be adapted in accordance with examples of the present invention. The system 1100 comprises one or more processing devices 1110 arranged to perform various processing functions. In some example embodiments, one or more of the processing devices 1110 may comprise one or more processor cores arranged to execute computer program code. Additionally/alternatively, at least one of the processing devices may comprise a hardware processing device, such as an application specific integrated circuit (ASIC) device or hardware accelerator module comprising hardware circuity arranged to perform predefined processing of data provided thereto.

The system 1100 further comprises one or more memory elements 1120. The memory element(s) 1120 may consist of one or more non-transitory computer program products such as, for example, a hard disk, an optical storage device such as a CD-ROM device, a magnetic storage device, a Read Only Memory, ROM, a Programmable Read Only Memory, PROM, an Erasable Programmable Read Only Memory, EPROM, an Electrically Erasable Programmable Read Only Memory, EEPROM, and a Flash memory, etc. The memory element 1120 may additionally/alternatively comprise one or more volatile memory elements such as, for example, Random Access Memory (RAM), cache memory, etc.

For simplicity and ease of understanding, a single processing device 1110 and a single memory element 1120 will hereinafter be referred to. However, it will be appreciated that such references to a single processing device 1110 or a single memory element 1120 are intended to encompass multiple processing devices 1110 and multiple memory elements 1120 respectively.

The memory element 1120 may have stored therein executable computer program code to be executed by the processing device 1110. The memory element 1120 may further have stored therein data to be accessed and/or processed by the processing device 1110 when executing computer program code.

The system 1100 illustrated in FIG. 11 further comprises one or more output devices, indicated generally at 1130. Such output devices may comprise, by way of example, a display device, a printer device, a network interface device, etc. The system 1100 illustrated in FIG. 11 further comprises one or more user input devices, indicated generally at 1140. Such input devices may include, by way of example, a keyboard, a keypad, a mouse, a touchscreen, etc. In accordance with some examples of the present invention, the processing device 1110 is arranged to generate quantitative data for biliary tree structures from volumetric medical imaging scan data, for example in accordance with the various methods hereinbefore described with reference to the accompanying drawings. Accordingly, the processing device 1110 is arranged to:

perform segmentation of a volume of the medical imaging scan data to identify tubular biliary structures within the volume of the medical imaging scan data;

compute a set of quantitative structural parameters for each location along the lengths of identified tubular biliary structures; and output quantitative biliary tree data comprising the sets of quantitative structural parameters for the identified tubular biliary structures.

For example, the processing device 1110 may be arranged to execute computer program code stored within the memory element 1120 for performing at least some of the steps of the various methods hereinbefore described with reference to the accompanying drawings.

As illustrated in FIG. 11, the image processing system 1100 may be operably coupled to at least one data storage device 1150 from which the processing device 1110 is able to retrieve imaging scan data, and to which the processing device 1110 may be able to output the quantitative biliary tree data comprising the set of quantitative structural parameters for the segmented tubular biliary structures. It is further contemplated that the various values, metrics, measures and other data generated by the image processing system 1100 in generating the quantitative biliary tree data may also be output to and stored within the data storage device 1150, either collectively or separately, such data including, by way of example only:

Hessian volumes;
Eigenvectors;
$R_a$ ratios;
$R_b$ ratios;
Intensity metrics S;
Tubular measures ($T_o/T_o(\sigma)$);
Scales ($\sigma$);
Segmented (binarized) volumes
Centre-line points;
Tube-width estimations;
Branch nodes;
Medialness values;
Stricture and/or dilatation data; and
Detected inflammation and fibrosis in the proximity of the biliary tree structure.

Figure 12:
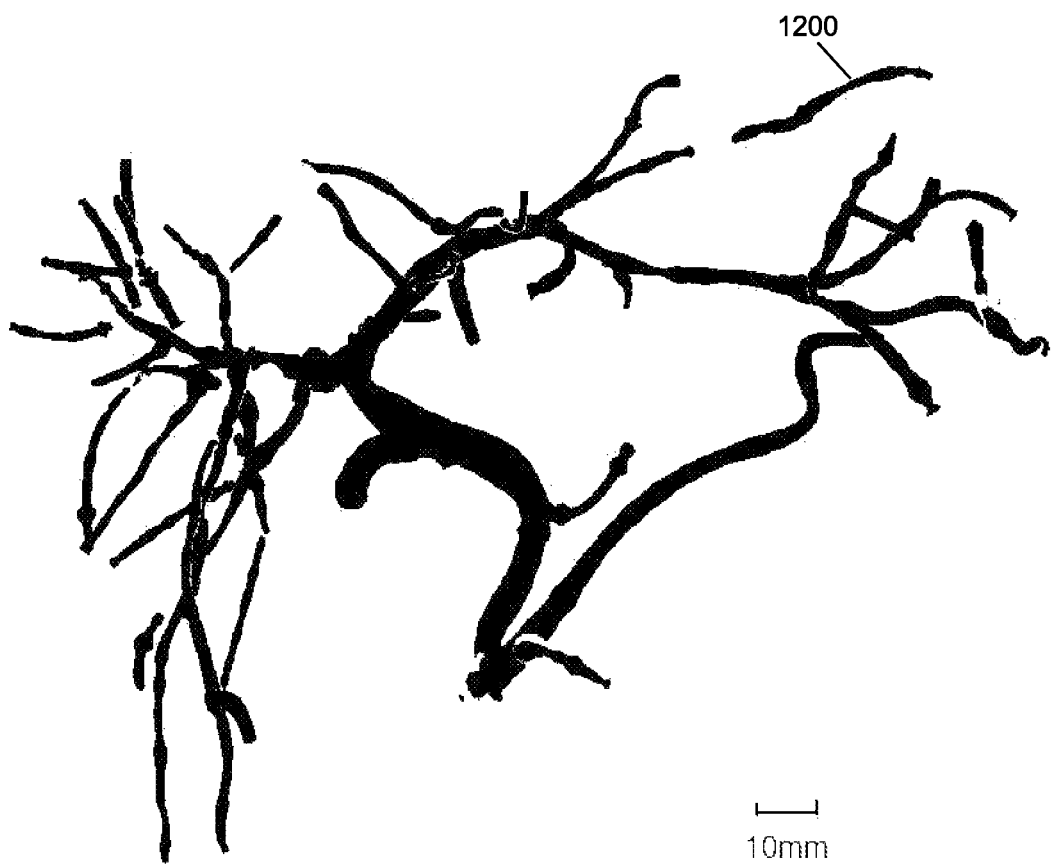
FIG. 12 illustrates a 3D-rendered quantitative model of the biliary tree of a patient with primary sclerosing cholangitis.

FIG. 12 illustrates a 3D-rendered quantitative model of the biliary tree 1200 of a patient with primary sclerosing cholangitis. The diameters of the branches correspond to the diameters of the biliary ducts following segmentation of the MRCP scan and subsequent parametric modelling of the identified tubular structures.

As described above, the invention may be implemented in a computer program for running on an image processing system, at least including code portions for performing steps of a method according to the invention when run on a programmable apparatus, such as an image processing system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media (e.g., CD-ROM, CD-R, etc.) and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

We claim:

1. A method of generating quantitative data for biliary tree structures from volumetric medical imaging scan data; the method comprising:
    performing tubular enhancement on the volumetric medical imaging scan data to derive at last one tubeness measure for each voxel within the volumetric medical imaging scan data;
    performing segmentation of a volume of the medical imaging scan data to identify tubular biliary structures within the volume of the medical imaging scan data based at least partly on the at least one tubeness measure for each voxel;
    for at least one segmented tubular biliary structure within the volume of the medical imaging scan data, computing at least one set of quantitative structural parameters for at least one location along the length of the tubular biliary structure; and
    outputting quantitative biliary tree data comprising the at least one set of quantitative structural parameters for the at least one segmented tubular biliary structure.

2. The method of claim 1, wherein the set of quantitative structural parameters comprises at least one parameter representative of at least one of:
    a centre-line position of the at least one segmented tubular biliary structure at the at least one location;
    a centre-line orientation of the at least one segmented tubular biliary structure at the at least one location;
    a radius of the at least one segmented tubular biliary structure at the at least one location;
    a diameter of the at least one segmented tubular biliary structure at the at least one location;
    a cross-sectional orientation of the at least one segmented tubular biliary structure at the at least one location;
    a cross-section profile of the at least one segmented tubular biliary structure at the at least one location;
    an indication of the presence of a branching point for the at least one segmented tubular biliary structure at the at least one location; and an orientation of a branching point for the at least one segmented tubular biliary structure at the at least one location.

3. The method of claim 1, wherein the method comprises determining centre-line positions at a plurality of locations along the length of the at least one segmented tubular biliary structure.

4. The method of claim 3, wherein determining centre-line positions for the at least one segmented tubular biliary structure comprises:
identifying a starting centre-line point for the at least one segmented tubular biliary structure;
identifying an ending centre-line point for the at least one segmented tubular biliary structure; and
incrementally from the starting centre-line point, determining successive centre-line points for the at least one segmented tubular biliary structure until the ending centre-line point is reached.

5. The method of claim 4, wherein a successive centre-line point is determined by:
identifying a set of viable successor points;
evaluating a cost function for each point within the set of viable successor points; and
selecting a successive centre-line point from the set of viable successor points based on the cost functions therefor.

6. The method of claim 3, wherein the method further comprises, for each of the plurality of locations along the length of the at least one segmented tubular biliary structure, determining a tube-width estimation for the at least one segmented tubular biliary structure.

7. The method of claim 6, wherein the tube-width estimation for each location is computed by determining a cross-sectional orientation of the at least one segmented tubular biliary structure at the respective location and determining a tube-width estimation for the at least one segmented tubular biliary structure in the determined cross-sectional orientation.

8. The method of claim 6, wherein the method further comprises detecting patterns of change within the at least one segmented tubular structure based on the tube-width estimations along the length of the at least one segmented tubular structure.

9. The method of claim 8 wherein the method comprises detecting patterns of change within the at least one segmented tubular structure by applying at least one pattern detection window to the tube-width estimation data.

10. The method of claim 8 wherein the method comprises detecting at least one of:
strictures;
dilatations; and
beading.

11. The method of claim 1, wherein the method comprises:
identifying a first tubular biliary structure within the volume of the medical imaging scan data;
determining branch node locations along the length of the first tubular biliary structure; and
identifying further tubular biliary structures branching off from the branch nodes along the length of the first tubular biliary structure.

12. The method of claim 11, wherein the method comprises recursively identifying further tubular biliary structures branching off from identified tubular biliary structures to derive a hierarchical biliary tree structure.

13. The method of claim 12, wherein the method comprises computing at least one set of quantitative structural parameters for each location along the length of each identified tubular biliary structure.

14. The method of claim 1, wherein the tubular enhancement comprises, for each voxel within the volume of the medical imaging scan data, computing at least one metric distinguishing tubular structures from other structures and computing a tubeness measure for the respective voxel based at least partly on the at least one metric.

15. The method of claim 14, wherein the tubular enhancement comprises, for each voxel within the volume of the medical imaging scan data, computing a first metric distinguishing tubular structures from spherical structures and a second metric distinguishing tubular structures from plate-like structures, and computing a tubeness measure for the respective voxel based at least partly on the first metric, the second metric and a scan intensity value for the respective voxel.

16. The method of claim 1, wherein the method comprises using multi-scale Hessian based tubular biliary structure enhancement.

17. The method claim 1, wherein the volumetric medical imaging scan data comprises imaging scan data obtained via a magnetic resonance imaging modality.

18. An image processing system arranged to generate quantitative data for biliary tree structures from volumetric medical imaging scan data, the image processing system comprising at least one processing device arranged to:
perform tubular enhancement on the volumetric medical imaging scan data to derive at least one tubeness measure for each voxel within the volumetric medical imaging scan data perform segmentation of a volume of the medical imaging scan data to identify tubular biliary structures within the volume of the medical imaging scan data based at least partly on the at least one tubeness measure for each voxel;
for at least one segmented tubular biliary structure within the volume of the medical imaging scan data, compute at least one set of quantitative structural parameters for at least one location along the length of the tubular biliary structure; and
output quantitative biliary tree data comprising the at least one set of quantitative structural parameters for the at least one segmented tubular biliary structure.

19. The image processing system of claim 18, wherein the set of quantitative structural parameters comprises at least one parameter representative of at least one of:
a centre-line position of the at least one segmented tubular biliary structure at the at least one location;
a centre-line orientation of the at least one segmented tubular biliary structure at the at least one location;
a radius of the at least one segmented tubular biliary structure at the at least one location;
a diameter of the at least one segmented tubular biliary structure at the at least one location;
a cross-sectional orientation of the at least one segmented tubular biliary structure at the at least one location;
a cross-section profile of the at least one segmented tubular biliary structure at the at least one location;
an indication of the presence of a branching point for the at least one segmented tubular biliary structure at the at least one location; and
an orientation of a branching point for the at least one segmented tubular biliary structure at the at least one location.

20. The image processing system of claim 18, wherein the at least one processing device is arranged to determine centre-line positions at a plurality of locations along the length of the at least one segmented tubular biliary structure.

21. The image processing system of claim 20, wherein the at least one processing device is arranged to determine centre-line positions for the at least one segmented tubular biliary structure by:
   identifying a starting centre-line point for the at least one segmented tubular biliary structure;
   identifying an ending centre-line point for the at least one segmented tubular biliary structure; and
   incrementally from the starting centre-line point, determining successive centre-line points for the at least one segmented tubular biliary structure until the ending centre-line point is reached.

22. The image processing system of claim 21, wherein the at least one processing device is arranged to determine a successive centre-line point by:
   identifying a set of viable successor points;
   evaluating a cost function for each point within the set of viable successor points; and
   selecting a successive centre-line point from the set of viable successor points based on the cost functions therefor.

23. The image processing system of claim 20, wherein the at least one processing device is further arranged to, for each of the plurality of locations along the length of the at least one segmented tubular biliary structure, determine a tube-width estimation for the at least one segmented tubular biliary structure.

24. The image processing system of claim 23, wherein at least one processing device is arranged to compute the tube-width estimation for each location by determining a cross-sectional orientation of the at least one segmented tubular biliary structure at the respective location and determining a tube-width estimation for the at least one segmented tubular biliary structure in the determined cross-sectional orientation.

25. The image processing system of claim 23 wherein the at least one processing device is further arranged to detect patterns of change within the at least one segmented tubular structure based on the tube-width estimations along the length of the at least one segmented tubular structure.

26. The image processing system of claim 25, wherein the at least one processing device is further arranged to detect patterns of change within the at least one segmented tubular structure by applying at least one pattern detection window to the tube-width estimation data.

27. The image processing system of claim 25 wherein the at least one processing device is arranged to detect at least one of:
   strictures;
   dilatations; and
   beading.

28. The image processing system of claim 18, wherein the at least one processing device is arranged to:
   identify a first tubular biliary structure within the volume of the medical imaging scan data;
   determine branch node locations along the length of the first tubular biliary structure; and
   identify further tubular biliary structures branching off from the branch nodes along the length of the first tubular biliary structure.

29. The image processing system of claim 28, wherein the at least one processing device is arranged to recursively identify further tubular biliary structures branching off from identified tubular biliary structures to derive a hierarchical biliary tree structure.

30. The image processing system of claim 29, wherein the at least one processing device is arranged to compute at least one set of quantitative structural parameters for each location along the length of each identified tubular biliary structure.

31. The image processing system of claim 18, wherein the at least one processing device is arranged to perform tubular enhancement comprising, for each voxel within the volume of the medical imaging scan data, computing at least one metric distinguishing tubular structures from other structures and computing a tubeness measure for the respective voxel based at least partly on the at least one metric.

32. The image processing system of claim 31, wherein the at least one processing device is arranged to perform tubular enhancement comprising, for each voxel within the volume of the medical imaging scan data, computing a first metric distinguishing tubular structures from spherical structures and a second metric distinguishing tubular structures from plate-like structures, and computing a tubeness measure for the respective voxel based at least partly on the first metric, the second metric and a scan intensity value for the respective voxel.

33. The image processing system of claim 18, wherein the at least one processing device is arranged to use multi-scale Hessian based tubular biliary structure enhancement.

34. The image processing system of claim 18, wherein the volumetric medical imaging scan data comprises imaging scan data obtained via a magnetic resonance imaging modality.

35. The method of claim 1, wherein the method is performed using a non-transitory computer program product having stored therein executable computer program code for generating quantitative data for biliary tree structures from volumetric medical imaging scan data.

36. The non-transitory computer program product of claim 35, wherein the non-transitory computer program product comprises one of a hard disk, an optical storage device, a magnetic storage device, a Read Only Memory, a Programmable Read Only Memory, an Erasable Programmable Read Only Memory, an Electrically Erasable Programmable Read Only Memory, and a Flash memory.

* * * * *